United States Patent [19]

Douchy et al.

[11] Patent Number: 4,656,007
[45] Date of Patent: Apr. 7, 1987

[54] PROGRAMMABLE AUTOMATIC MEANS FOR THE DEPOSITION IN A PRECISE POSITION OF A MINUTE, PRECISE QUANTITY OF LIQUID ON AN ANALYTICAL SUPPORT

[75] Inventors: Marc Douchy, Gif sur Yvette; Pierre Lohez, Paris; Jean-Guy Malecot, Longjumeau; Gilbert Retali, Colombes, all of France

[73] Assignee: Commissariat a l'Energie Atomique, Paris, France

[21] Appl. No.: 779,578

[22] Filed: Sep. 24, 1985

[30] Foreign Application Priority Data

Oct. 1, 1984 [FR] France .................................. 84 15048

[51] Int. Cl.$^4$ ........................................... G01N 35/04
[52] U.S. Cl. ..................................... 422/64; 222/309;
422/52; 422/63; 422/67; 422/99; 422/100;
422/102; 436/47; 436/180; 221/113; 221/119
[58] Field of Search ........................ 422/52, 63, 64, 67,
422/78, 80, 99, 100, 102; 222/309; 73/864.12,
864.14; 221/113, 119

[56] References Cited

U.S. PATENT DOCUMENTS 3,464,800  9/1969  Gerarde ............................. 422/100
3,525,264  8/1970  Nieglos et al. .................... 73/864.14
4,023,716  5/1977  Shapiro ............................. 222/309
4,181,700  1/1980  Chervenka et al. ................ 422/100
4,188,986  2/1980  Wetterlin et al. ..................... 422/64
4,224,032  9/1980  Glover et al. ........................ 436/46
4,287,155  9/1981  Tersteeg et al. ..................... 422/64
4,340,390  7/1982  Collins et al. ....................... 422/64

FOREIGN PATENT DOCUMENTS 2447751  10/1980  France ............................... 422/100

Primary Examiner—Michael S. Marcus

[57] ABSTRACT

Programmable automatic means for the depositing in a precise position on an analytical support of a precise, minute liquid quantity. It comprises a main support provided with displacement means, a piston syringe mounted on the main support, a distributor of a plurality of hollow sampling needles, a cutting device, a sample solution distributor with several recesses, an analytical support holder, an analytical support gripping means and extraction means, a distributor for new analytical supports, a receiver for analytical supports following the sample deposition and a used needle extractor.

This automatic means can be used in a system associated with a thermoionization mass spectrometry analysis apparatus.

3 Claims, 6 Drawing Figures

PROGRAMMABLE AUTOMATIC MEANS FOR THE DEPOSITION IN A PRECISE POSITION OF A MINUTE, PRECISE QUANTITY OF LIQUID ON AN ANALYTICAL SUPPORT

BACKGROUND OF THE INVENTION

The present invention relates to a programmable automatic means for the deposition in a precise position of a minute and precise quantity of liquid on an analytical or analysis support.

This automatic means is more particularly intended for supplying with successive samples deposited on supports to equipment for the successive analysis of a solution when the solution quantity to be deposited is of small volume (1 to 20 microliters).

This automatic means is also suitable for supplying equipment for analyzing solution samples, when it is not possible or not wished to use more than a small amount of the solution, which can e.g. be the case in medical analysis.

More specifically, the invention aims at providing a programmable automatic means simultaneously having all the following performance characteristics:

- the sample must be taken in a minute quantity of just a few small drops, with a high accuracy and total reproducibility of the number of drops;
- the taking of each successive sample from a container containing the solution to be analyzed must be carried out without contamination of one sample by the taking of the previous sample;
- the deposition of each sample on its associated support must be carried out very accurately and reproducibly for successive samples.

However, hitherto no such programmable automatic means having all these features is known.

Thus, the invention has the essential aim of proposing such a novel, automatic means.

SUMMARY OF THE INVENTION

To this end the invention relates to a programmable automatic means for carrying out the deposition in a precise position on an analytical support of a precise, variable and reproducible minute quantity of liquid, wherein it comprises in combination:

- a main support provided with displacement means enabling it to successively occupy at least five positions,
- a piston syringe mounted on the main support and provided with means for displacing said syringe relative to said main support, and means for grasping a hollow solution sampling needle by one of its ends and means for displacing the piston;
- a distributor of a plurality of hollow sampling needles provided with means for successively presenting each needle at a first location corresponding to the first position of the syringe-holder support, whereby prior to sampling the solution each hollow needle is new and has a length slightly exceeding the subsequent precise length,
- a cutting device placed in a second position corresponding to the second position of the syringe-holder suport for cutting a needle held by said syringe end gripping means to the precise length at a precise point in space, when the syringe-holder support is placed in its second position,
- a solution sample distributor having several recesses provided with means for successively presenting each recess at a third location corresponding to the third position of the syringe-holder support, each recess serving to receive a solution sample prior to a complete operating cycle of the automatic means,
- an analysis or analytical support holder provided with displacement means enabling it to occupy three positions, whereof the second corresponds to the fourth position of the syringe-holder support,
- a means for gripping the analytical supports and
- a means for extracting the analytical supports,
- a new analytical support distributor having a plurality of recesses, provided with means for successively presenting each analytical support at a location corresponding to the first position of said analytical support holder, each recess serving to receive a new analytical support before a complete operating cycle of the automatic means,
- a receiver for analytical supports following sample deposition having several recesses, provided with means for successively presenting each recess at a location corresponding to the third position of said analytical support holder, each recess of the receiver being left free prior to a complete operating cycle of the automatic means,
- a used needle extractor, placed at a location corresponding to the fifth position of the syringe-holder support, and
- per se known means in automatic equipment technology for actuating, programming and positioning the relative displacements and operations of the various devices and means referred to hereinbefore which, by their combination, form the aforementioned automatic means.

This automatic means essentially functions as follows. In its first position, the syringe holder makes the syringe grasp a new hollow needle. In its second position the syringe holder presents the end of said needle to the cutting device, which cuts the needle to a precise length. In the third syringe holder position, the syringe advances towards a recess in the sample distributor and introduces the new hollow needle into it. The syringe piston then moves back in order to such up a precise quantity of the sample solution to be analyzed. The complete syringe then moves back. In the fourth syringe holder position, the accurately cut end of the hollow needle filled with the sample liquid to be analyzed is positioned in a very precise position with respect to a new analytical support, which is then presented by an analytical support holder in the second position. The syringe piston advances stepwise in order to deposit an exact desired and reproducible number of sample drops on the analytical support. In the fifth syringe holder position, the syringe end is freed from the used needle. For its part and in time coordination, the analytical support holder takes up, in its first position, a new analytical support. In its second position, it places this new analytical support in front of the cut end of the liquid-filled needle in order to receive the precise, minute quantity of solution sample when the syringe holder is in its fourth position. Finally, in its third position, the analytical support holder places on the analytical support receiver an analytical support on which a deposit is to be made.

One of the essential features of the automatic means is based on the non-obvious choice made by producing the succession of hollow sampling needles, by successive cutting to the precise length of a sequence of small diameter, hollow tube elements. This overcomes the problem of length variation in commercially produced needles, so that certainty exists regarding the position in space of the needle end, which is indispensable for being able to very accurately position said end with respect to an analytical support.

According to a further secondary, but interesting feature, the syring is mounted on the main syringe-holder support via elastic means and the needle grasping end of the syringe is an outwardly widened conical shape and is provided with at least one friction O-ring.

As a result of these means, it is apparent that when the syringe holder is in its first position and the syringe advances towards the grasping location of a new hollow sampling needle of the needle distributor, the widened cone of the syringe end ensures the positioning of the needle inlet into said end and then the centering thereof. The needle then enters with friction the O-ring. The advance of the syringe continues and the needle end abuts to the bottom of its recess provided on the end of the syringe, as a result of the elastic mounting of the syring on the support. All this ensures a good fitting of a new needle on to the syringe end and prepares the necessary conditions for the subsequent cutting to the precise length of said needle and as indicated hereinbefore.

As a result of another secondary, but interesting feature, each sample distributor recess is a cylindrical recess whose bottom is provided with elastic means for freely receiving small corresponding container containing a sample, and the angle formed with the vertical by the common axis of the small container and its recess is greater than the angle formed with the vertical by the hollow sampling needle axis.

As a result of this feature, it is apparent that when the syringe advances towards a recess in the sample distributor, it is possible to ensure that the sampling needle end will abut at the lowest point of the small container containing the sample, and will take a few drops of said sample, even if there is only a very small quantity of liquid in the small container.

BRIEF DESCRIPTION OF THE DRAWINGS

The invention is described in greater detail hereinafter relative to non-limitative embodiments and the attached drawings, wherein show.

DETAILED DESCRIPTION OF THE PREFERRED EMBODIMENTS

Figure 1:
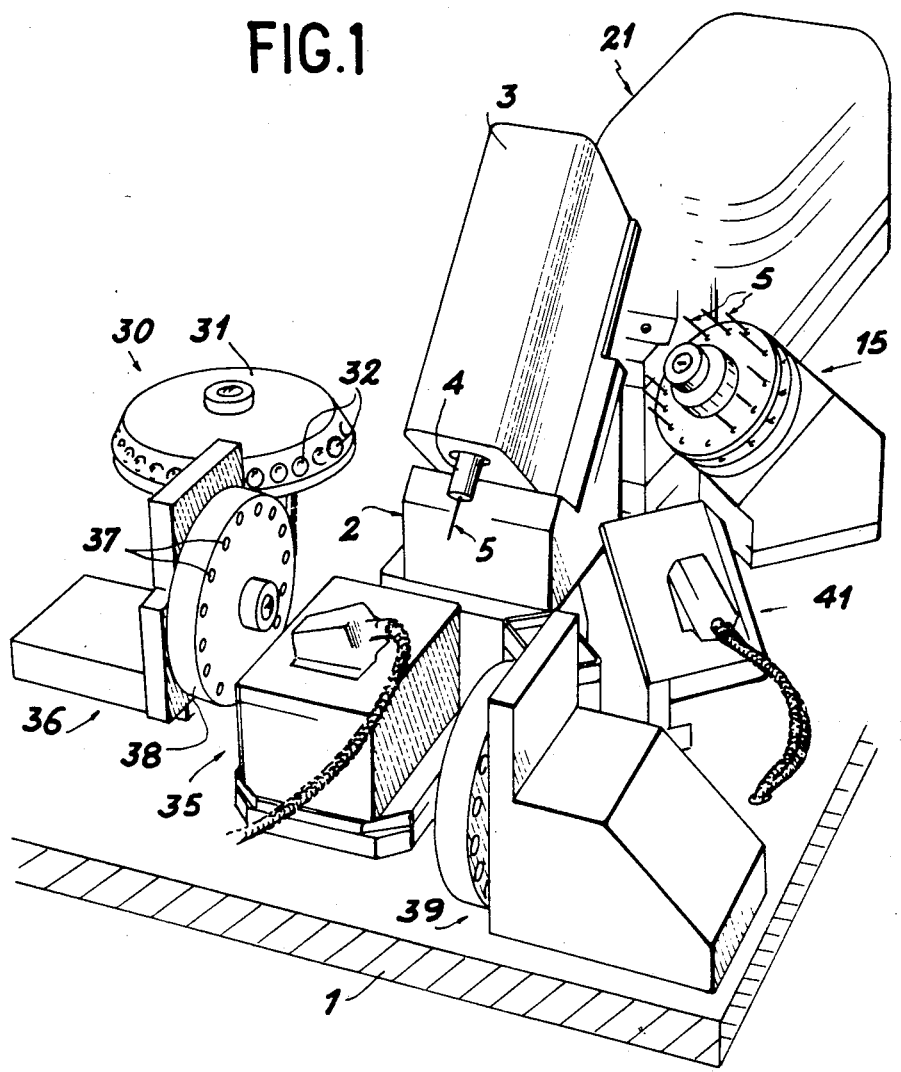
FIG. 1 in perspective, all the elements forming the programmable automatic means according to the invention.
Figure 2:
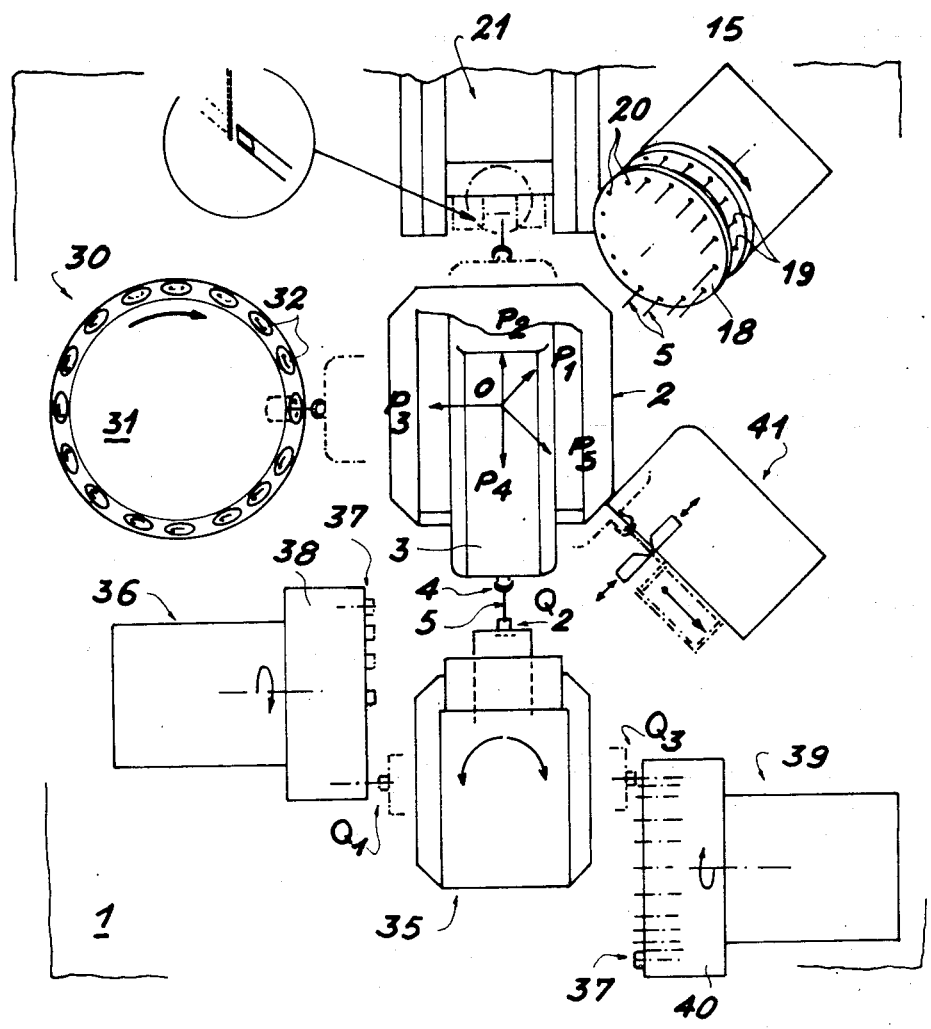
FIG. 2 diagrammatically, in plan view, said same group of components.

A description will firstly be given of all the components of the automatic syringe shown in FIGS. 1 and 2. This automatic means described in exemplified manner, is part of a system associated with a thermoionization mass spectrometry analysis apparatus for determining the isotopic compositions of solids and chemical concentrations by isotopic dilution.

For the study of solids by thermoionization mass spectrometry, it is necessary to deposit on one of the filaments of a three-filament support member, small quantities ($10^{-2}$ to 10 microgrammes) of the element to be studied.

The procedure used consists of placing in an acid solution (generally 0.2N nitric acid) the element to be studied and depositing on the filament chosen a few microliters (1 to 10) of said solution. The solution is deposited in fractions (e.g. 0.5 microliter) whilst evaporating to dryness, between each fraction deposited, by passing an electric current through the filament in question. At the end of deposition, the filament is heated, by the passage of an electric current, followed by a given procedure for bringing the deposit into the most suitable chemical state for analysis.

The two other filaments, which are then connected in series, are slightly heated by the passage of an electric current, to prevent any condensation of the product on the surface thereof.

This procedure is used in fuel reprocessing plants and then leads to the deposition of active solutions.

It is in the perspective of a total automation of mass spectrometry, more particularly used in reprocessing plants, that the automatic means for "automatic depositions" carrying out all the aforementioned operations is developed. This automatic means has several significant advantages. Thus, it makes it possible to significantly reduce the radiation exposure risk to personnel, avoids the need for operators to carry out tiresome, repetitive operations, improves the reproducibility of deposits, ensures a better utilization of the mass spectrometer.

This automatic means comprises a system of mechanical elements, controlled from a microprocessor card via interface frames. A printer permits a dialogue with the automatic means. The active elements of the automatic means are obviously installed in a tight enclosure (glove box).

In view of the activity and chemical corrosiveness of the solutions deposited and in order to facilitate the handling thereof, all the mechanical components which can placed outside the glove box are positioned there and the movements are then transmitted by tight passages. The components placed within the enclosure, constituted easily dismantlable and removable modules, they are covered and protected by air scavenging, with distribution of fresh scavenging air of the box at each module.

The elements necessary for the electrical supply, control and command of the robot are placed in an electronic bay.

All the means necessary for nuclearization of any apparatus used in a radioactive medium are known in nuclear technology and will not be described in detail here. However, a detailed description will be given of the various mechanical components of the automatic means and its operation procedure.

The central part of the automatic means mounted on a workbench 1 is a main support constituted by a turret 2, provided with rotation means enabling it to successively occupy five positions around centre 0 (FIG. 2), resprectively P1, P2, P3, P4 and P5.

A syringe holder 3, carrying a syringe 4 and terminated by a needle 5, is mounted in mobile manner on turret 2 so as to permit, for each position of the turret P1, P2, P3, P4 or P5, an advance or return of the syringe 4 and its needle 5 with respect to the different locations of operations to be performed, corresponding to these five positions as will be described hereinafter.

Figure 3:
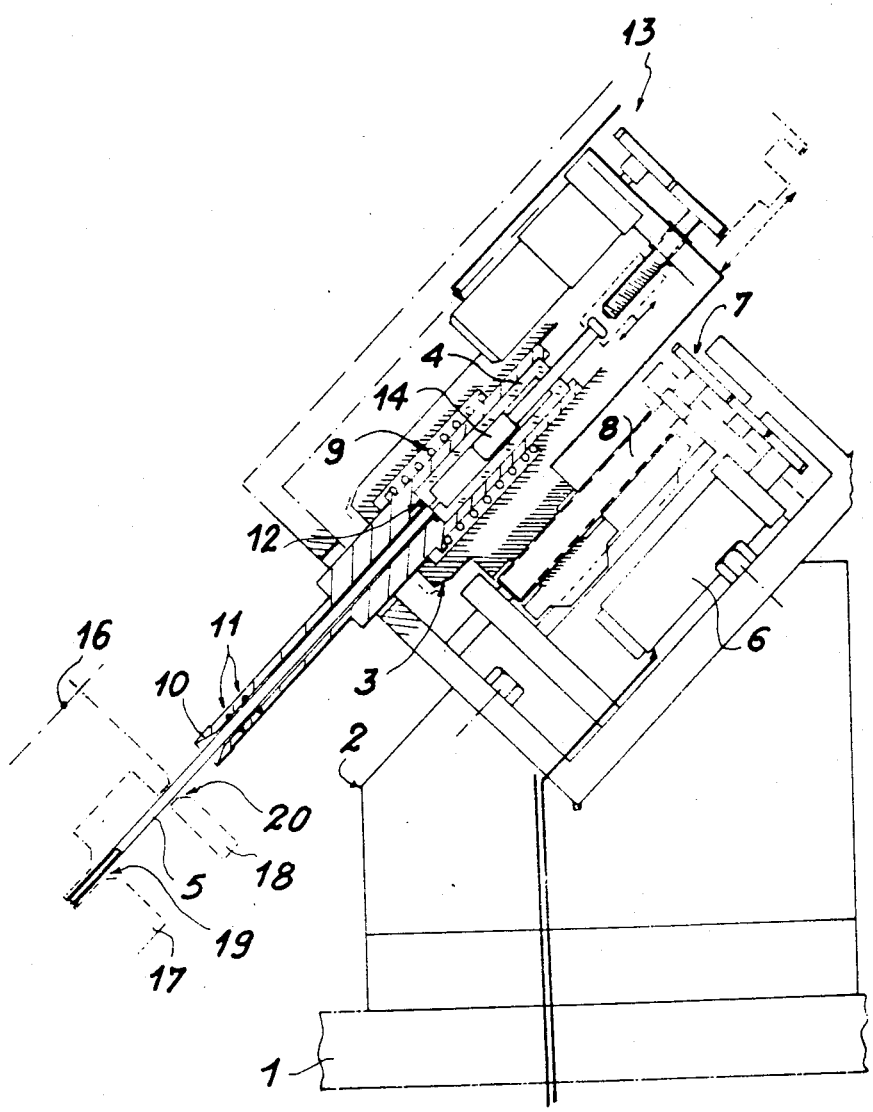
FIG. 3 diagrammatically and in section a syringe holder.

The syringe holder is shown in greater detail in FIG. 3, where it is possible to see the turret 2 on which is mounted the syringe holder 3. The latter is mobile on turret 2 for advance and return movements as a result of the action of a motor 6, and a reduction gear 7, actuating a threaded bar 8 controlling said movements of the syringe holder in slides provided for this purpose. The actual syringe 4 is mounted on its syringe holder 3 by elastic means indicated by spring 9.

The front end 10 of the syringe has an outwardly widened conical shape and is equipped with two friction O-rings 11. As stated hereinbefore, these means are responsible for the guidance at the syringe entrance of the needle end when the syringe approaches said end, the centering of the needle and its grasping and holding by O-rings 11. When the advance movement of the syringe towards the needle continues, the needle head finally abuts on the syringe shoulder 12 and a supplementary advance of the syringe leads to a displacement thereof with respect to syringe holder 3 as a result of the compression of spring 9. A geared motor 13 makes it possible to displace piston 14 within syringe 4.

Figure 4:
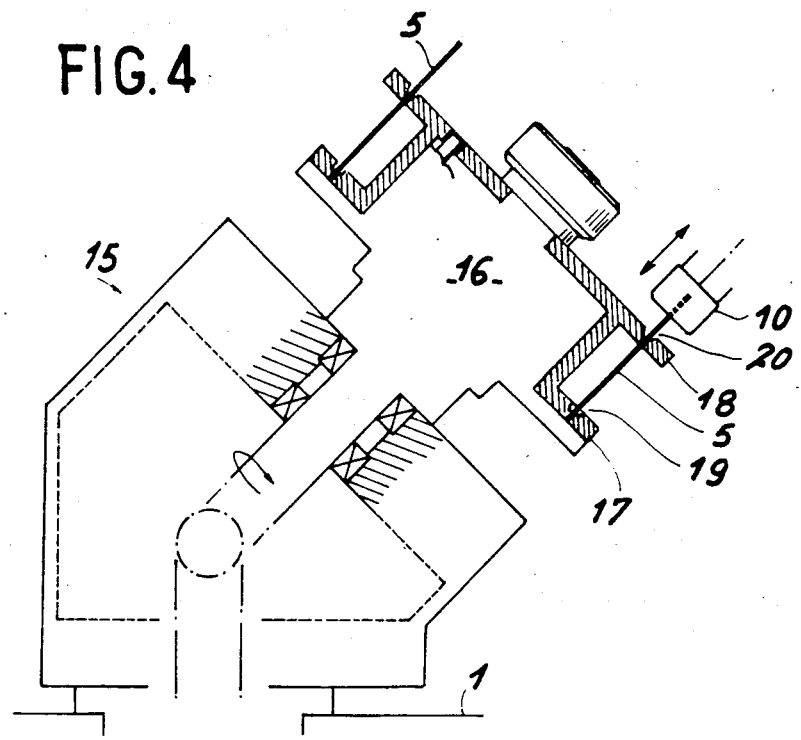
FIG. 4 diagrammatically and in section a needle distributor.

The automatic means also comprises a distributor for a plurality of hollow sampling needles 15 in FIGS. 1 and 2 and shown in greater detail in FIG. 4. According to this example, this distributor essentially comprises a journal 16 having a circular base ring 17 and a circular flange 18 perforated by a respective series of recesses 19 and holes 20 in several positions, e.g. 32 thereof.

Prior to a complete operating cycle the automatic means, the needle distributor 15 is loaded with 32 new hollow needles 5, having a length slightly greater than the consequently precise length, as will be shown hereinafter. The gripping of the needle takes place when the central turret 2 is oriented towards its position P1 and as can be desribed relative to FIG. 3.

Figure 5:
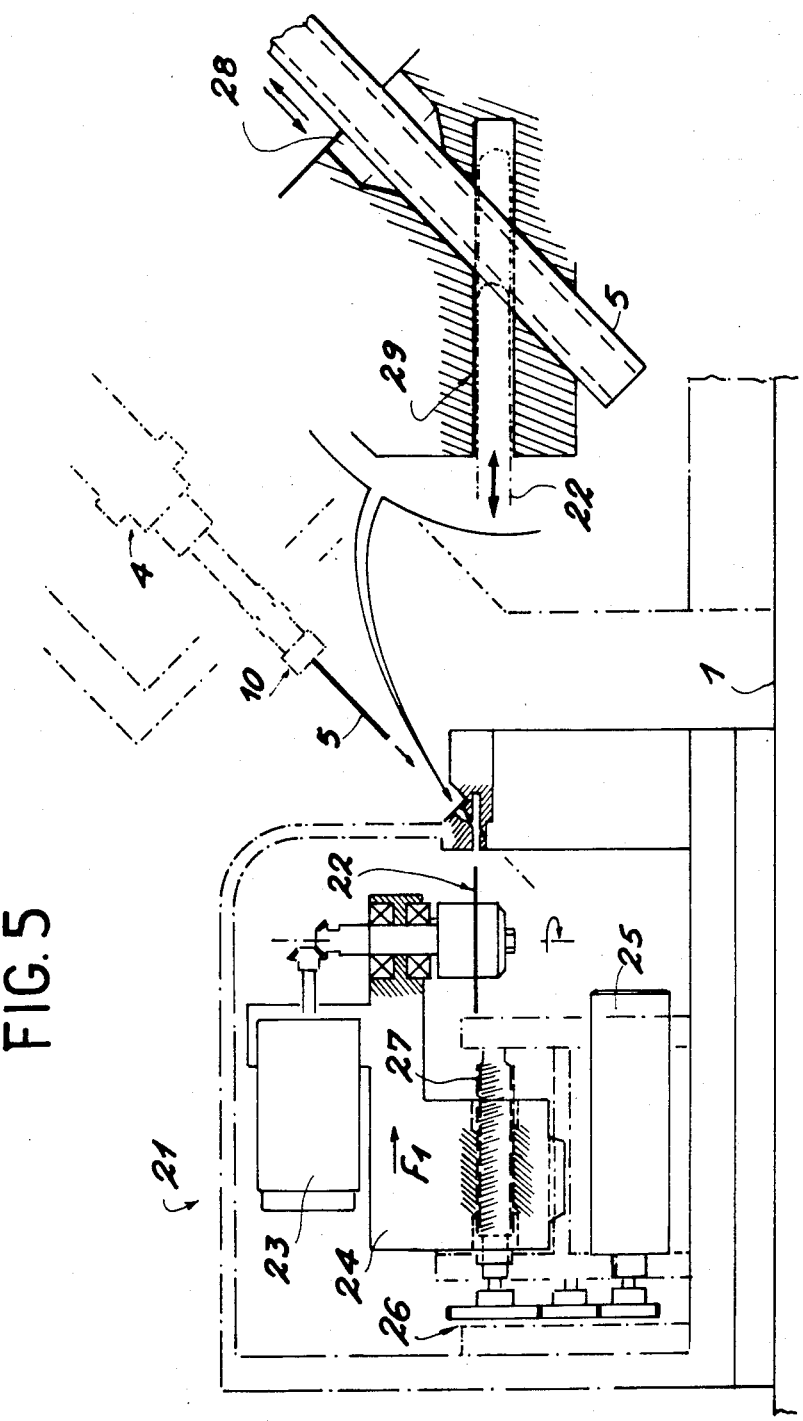
FIG. 5 diagrammatically and in section a device for cutting a hollow sampling needle to a precise length.

The automatic means also comprises a needle cutting device 21 in FIGS. 1 and 2 and shown in greater detail in FIG. 5. This device cooperates with the syringe holder turret 2, when the latter is oriented in its position P2. The cutting device 21 essentially comprises the rotary cutter 22, driven by a motor 23 mounted on a support 24 and able to move forward or back under the control of a motor 25, driving by a reduction gear 26 a threaded bar 27 controlling the movements thereof.

When the turret is in position P2 and the syringe holder 3 advances towards the bottom in accordance with the orientation of its axis inclined by 45°, the rough end of the new needle 5, which was grasped just beforehand in the manner described hereinbefore, is introduced into an appropriate guidance recess at the frustum-shaped inlet 28 of the cutting device, whereof a larger scale detail is shown to the right of FIG. 5. The cutter is then in the extreme left position as shown in FIG. 5. When the new, rough needle is introduced down to the bottom, motor 23 is started up and rotates the cutter 22 and the group of members 25, 26, 27 moves to the right, as indicated by arrow f1. Cutter 22 penetrates and advances in the guidance slot 29 in order to bring about a bevel cut at a precise point in space of the end of needle 5. The cutter then returns to the left position and the syringe holder withdraws to the rear the needle cut to the precise length.

Figure 6:
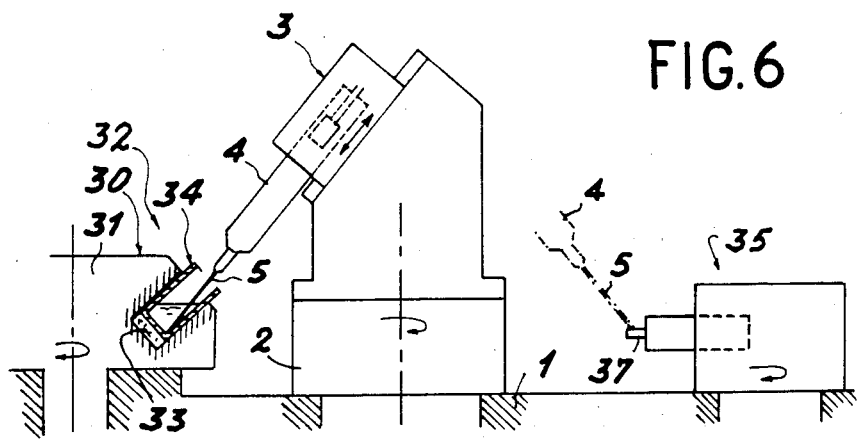
FIG. 6 diagrammatically and in section the relative positions of the syringe-holder support with respect to the sample distributor and the analytical support holder for the successive operations corresponding to these two positions.

The automatic means also comprises a distributor 30 for the successive samples to be analyzed, cf. FIGS. 1 and 2 and diagrammatically shown in section in FIG. 6. This sample distributor which cooperates with the syringe holder 22 when the latter is oriented in its position P3, essentially comprises a vertically axed circular journal 31, provided on its periphery with a plurality, e.g. 32, of cylindrical recesses with an axis inclined by 60° relative to the vertical. Each recess 32 is provided with a flexible elastic coating 33 on its bottom. The liquid sample is oontained in small glass containers 34.

Before a complete analytical sample, the sample distributor 30 is filled with these thirtytwo small containers 34.

The relative slope of the axes of needle 5 and containers 34 resting on the elastic bases 33 of recess 32 ensures that the sampling needle end 5 will, at the end of the travel of syringe 4, be positioned at the lowest point of container 34. This ensures the good takeup of sample, even if container 34 only contains a very small amount of this. More specifically, the descent axis of the needle intersects the base plane of container 34 at the bottom point thereof.

The syringe piston 14 then rises by n steps, a step corresponding to e.g. 0.5 microliter and the maximum number of steps n being 15, i.e. corresponding to 7.5 microliters. The syringe rises and then moves back. To be certain of restoring all the sampled solution, a prior moving back of the piston prior to sampling makes it possible to lower the latter again to a position lower than that at the start of sampling.

The needle which abuts against the bottom of the container leads to an elastic moving back of the syringe, but does not modify the position of the needle in the inoperative state. The number of sampling steps is limited by the needle capacity to prevent any pollution of one sample by the preceding samples (needle used once only, the only sampling element in contact with the solution to be deposited).

The automatic means is then positioned in position P4 facing an analytical support holder 35 in FIGS. 1, 2 and 6 (to the right of the latter). This analytical support holder 35 is provided with rotation means enabling it to successively occupy a first position P1 (FIG. 2) facing a new analytical support distributor 36. In the special application described, these analytical supports 37 are source support filaments for thermoionization mass spectrometry.

In another application, e.g. a medical application, they could be glass deposition plates. In all cases, the analytical support distributor 36 could be of a type having a journal 38 with a plurality of positions, 32 in this example.

When the analytical support holder 35 has grasped, in its first position P1, an analytical support 37, it then turns to position itself in position P2, corresponding to position P4 of the syringe holder turret 2, as diagrammatically shown in the right-hand part of FIG. 6. Syringe holder 3 advances towards the filament holder 35 and syringe 4 moves down.

By regulating the advance abutments of the syringe holder and filament holder, with the syringe in the bottom position, it is possible to bring about coincidence between the centre of the end of needle 5 and the centre of the filament. Piston 14 drops by one step, forming a drop which touches the filament at the end of needle 5. The syringe 4 rises again leaving a drop on the filament. The filament is heated to evaporate the drop. The syringe is lowered again and so on. If sampling involves n steps, deposition takes place over n+3 steps, so that it is certain that all the solution to be deposited is restored on the filament. The first two descent steps of the piston are used for recovering the mechanical clearances compensating the capillarity phenomena in the needle. Thus, the drop only appears at the third step. With the deposit completed at the n+3rd step and the syringe in the raised position, the reheating required by the operator takes place. The syringe holder 3 and filament holder 35 are then moved back.

With regards to the analytical support holder 35, it is then oriented towards it position P3 (FIG. 2) facing an analytical support extractor 39 following the deposition on said support of a solution sample to be analyzed.

This receiver has a multi-position journal 40, 32 in the present example, which are successively presented in position P3 of the analytical support holder 35 for receiving the support following sample deposition.

With regards to the syringe holder turret 2, following the deposition of the solution sample, on its support in positon P4, it is then oriented towards its position P5 to cooperate with a used needle extractor 41, which removes the used needle from the used end.

All the components of the automatic means described hereinbefore are combined with a group of end of travel abutments actuating switches indicating the physical states of locations of said components. Moreover, per se known means actuate and program the relative displacements and operations of the various devices and means which, in combination, constitute the programmable automatic means according to the invention. It appears that compared with the specific embodiment described hereinbefore, numerous variants are possible with regards to particular components of the automatic means, but whilst retaining the fundamental inventive idea of combining functional means so as to provide the basic design thereof.

What is claimed is:

1. A programmable automatic means for carrying out the deposition of a precise position on an analytical support of a minute, precise quantity of liquid, wherein it comprises in combination:
    a main support provided with displacement means enabling said support to successively occupy at least five positions,
    a piston syringe having a piston, is mounted on the main support and provided with means for displacing said syringe relative to said main support, said piston syringe having means for gripping one end of a hollow solution sampling needle and means for displacing the piston
    a distributor for holding a plurality of hollow sampling needles provided with means for successively presenting each needle at a first location corresponding to a first position of the syringe-holder support, said hollow needle distributor having a plurality of hollow needles, each hollows needle having a length slightly exceeding a predetermined length,
    a cutting device placed in a second position corresponding to a second position of the syringe-holder support for cutting a needle held by said syringe end gripping means to a predetermined length when the syringe holder support is placed in its second position,
    a solution sample distributor having several recesses provided with means for successively presenting each recess at a third location corresponding to a third position of the syringe-holder support, each recess serving to receive a solution sample prior to a complete operating cycle of the automatic means,
    an analytical support holder provided with displacement means enabling it to occupy three positions, whereof a second position corresponds to a fourth position of the syringe-holder support,
    a means for gripping the analytical supports and a means for extracting the analytical supports,
    a new analytical support distributor having a plurality of recesses, provided with means for successively presenting each analytical support at a location corresponding to a first position of said analytical support holder, each recess serving to receive a new analytical support before a complete operating cycle of the automatic means,
    a receiver for analytical supports following sample deposition having several recesses, provided with means for successively presenting each recess at a location corresponding to a third position of said analytical support holder, each recess of the receiver being left free prior to a complete operating cycle of the automatic means,
    a used needle extractor, placed at a location corresponding to a fifth position of the syringe-holder support, and
    control means for actuating and controlling said mainsupport, piston syringe and hollow needle gripper, said hollow needle distributor, said cutting device, said sample distributor, said analytical support holder, gripper, distributor and receiver, and said needle extractor whereby samples are accurately transferred for analysis.

2. A programmable automatic means according to claim 1, wherein the piston syringe is mounted on the main syringe-holder support via elastic means and wherein the needle gripping means is located at an end of the piston syringe has an outwardly widened conical shape and is provided with at least one friction O-ring.

3. A programmable automatic means according to claim 1, wherein each recess of the sample distributor has a cylindrical recess, with a bottom provided with elastic means for freely receiving a small corresponding container containing a sample and wherein an angle formed by a common axis of a small container and its recess with a vertical is greater than an angle formed by an axis of the hollow sampling needle with the vertical.

* * * * *